(12) United States Patent
Crocker

(10) Patent No.: US 8,113,043 B2
(45) Date of Patent: Feb. 14, 2012

(54) DOWNHOLE FLUID PROPERTY CHROMATOGRAPHY

(75) Inventor: Hugh Crocker, Welshpool (AU)

(73) Assignee: Crocker Research Pty Ltd, Welshpool, W.A. (AU)

( * ) Notice: Subject to any disclaimer, the term of this patent is extended or adjusted under 35 U.S.C. 154(b) by 61 days.

(21) Appl. No.: 12/312,718

(22) PCT Filed: Nov. 23, 2007

(86) PCT No.: PCT/AU2007/001804
§ 371 (c)(1),
(2), (4) Date: Jul. 16, 2009

(87) PCT Pub. No.: WO2008/064402
PCT Pub. Date: Jun. 5, 2008

(65) Prior Publication Data
US 2010/0064795 A1 Mar. 18, 2010

(30) Foreign Application Priority Data
Nov. 27, 2006 (AU) ............... 2006906639

(51) Int. Cl.
E21B 49/00 (2006.01)
(52) U.S. Cl. .................................... 73/152.23
(58) Field of Classification Search .................. None
See application file for complete search history.

(56) References Cited

U.S. PATENT DOCUMENTS

| | | | | |
|---|---|---|---|---|
| 3,196,664 A * | 7/1965 | Teal | ............. | 73/23.38 |
| 3,257,847 A * | 6/1966 | Levy et al. | ............. | 73/23.23 |
| 4,739,654 A * | 4/1988 | Pilkington et al. | ......... | 73/152.24 |
| 5,622,223 A * | 4/1997 | Vasquez | ............. | 166/264 |
| 6,581,441 B1 * | 6/2003 | Paul | ............. | 73/61.52 |
| 6,670,605 B1 * | 12/2003 | Storm et al. | ............. | 250/255 |
| 7,062,958 B2 * | 6/2006 | Diakonov et al. | ......... | 73/152.23 |
| 2003/0134426 A1 * | 7/2003 | Jiang et al. | ............. | 436/121 |

* cited by examiner

Primary Examiner — Robert Raevis
(74) Attorney, Agent, or Firm — The Nath Law Group; Jerald L. Meyer; Robert T. Burns

(57) ABSTRACT

A method for analyzing properties of fluids contained in a geological formation including the steps of lowering a tool containing a chromatograph down to a location within the geological formation; setting the tool into position; extracting a sample of formation fluid from the location within the geological formation under controlled conditions and directing it into the chromatograph; and analyzing the composition of the formation fluid sample located downhole. The formation fluid sample is delivered to the chromatograph with or without admixture with a solvent. A sampling tool for use in the method forms another aspect of the invention.

16 Claims, 2 Drawing Sheets

DOWNHOLE FLUID PROPERTY CHROMATOGRAPHY

Figure 1:
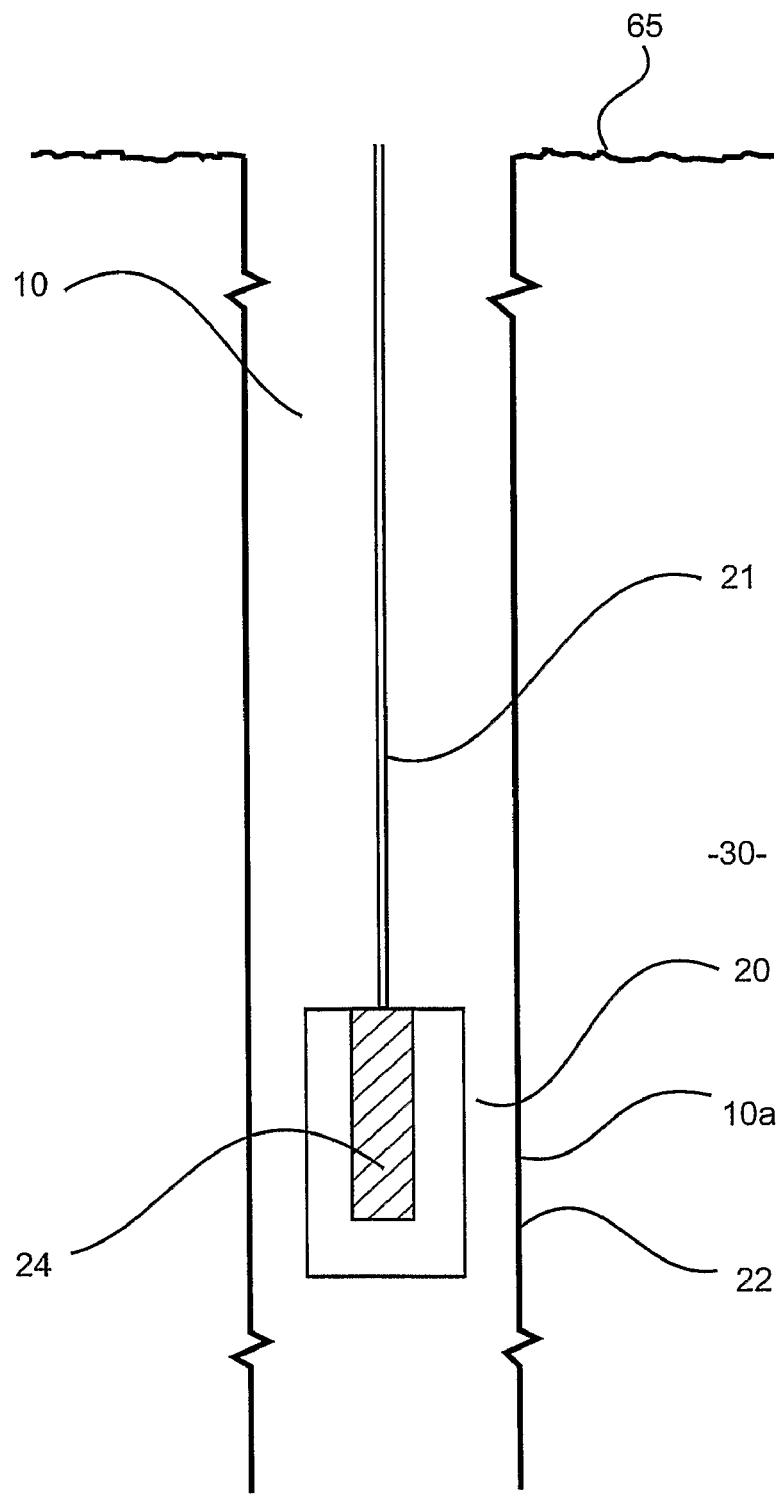

This is a national phase Application of PCT/AU2007/001804, filed 23 Nov. 2007, claiming priority from AU Application No. 2006 906639, filed 27 Nov. 2006, the entire content of which is hereby incorporated by reference in its entirety.

This invention relates to a method and tool for analysing properties of fluids contained within a geological formation.

Oil and gas exploration is aimed at finding geological formations or reservoirs containing hydrocarbons for commercial exploitation. Oil and gas explorers are constantly trying to find better, more reliable, faster and cheaper ways to assess the potential of prospective reservoir formations. Such a formation may be a folded rock formation, such as an anticline, that traps and holds hydrocarbons. The reservoir rock must be permeable and porous to hold hydrocarbons which are trapped in the reservoir by neighbouring impervious rock. Conventional well testing involving analysis of properties of fluids—especially hydrocarbon fluids—is a main part of that assessment. However, unless expensive bottom hole sampling devices are run during testing, only surface samples at a much lower pressure than the pressure of the reservoir can be obtained. These samples of oil and gas then require recombination to recreate a fluid sample that reflects the actual reservoir fluid under the reservoir conditions of pressure and temperature.

Down-hole formation fluid sampling tools are extensively used for oil and gas exploration and production. Sampling of fluids takes place at various locations within a borehole to provide analysis of fluids at each location. However, the sampling process is expensive and again may introduce error since fluid samples are not ordinarily tested until they are transferred to a surface analytical facility whether automated or not. Transfer always involves some loss of sample, usually gas, involving the volumes of small connecting tubes and regulators (valves). Sealing mechanisms such as valves, "o" rings and pistons are frequently subject to small losses. By this stage, changes in pressure and temperature as well as any mixture with solvents or other agents in preparation for testing may have changed the properties of the sample to the extent that an accurate analysis cannot be achieved. Such losses and changes in pressure and temperature may be particularly significant in their impact on hydrocarbon fluid analysis. Some formation fluids contain very dilute components, such as mercury that often go undetected but, on extended production, have very deleterious effect upon stainless steel production vessels. Similarly $H_2S$ gas reacts with the well completion steel and thus may not be accurately sampled. Other sulphur containing compounds, such as mercaptans, may also be problematic.

There are some tools that allow testing of fluid properties using instruments located down-hole. However, these instruments too induce changes in the fluid sample through admixture of fluid samples with solvents. Again, this can cause inaccuracy. Such inaccuracies may result in misleading characterisations of a fluid reservoir and this may result in poor reservoir evaluation and risk of wasted expense in exploitation of a less valuable reservoir. In the oil and gas industry, the expenses may be immense.

It is the object of the present invention to provide a method of analysing fluid properties less susceptible to errors caused by fluid transfer or instrument induced changes in fluid properties.

With this object in view, the present invention provides a method of analysing properties of fluids contained in a geological formation including the steps of:

a) lowering a tool containing a chromatograph down to a location within the geological formation;

b) setting the tool into position;

c) extracting a sample of formation fluid from the location within the geological formation under controlled conditions, and directing it into the chromatograph; and d) analysing the composition of the formation fluid sample located downhole;

wherein the formation fluid sample is delivered to the chromatograph with or without admixture with a solvent. Therefore, the sample can be extracted and introduced directly to the chromatograph, or to a carrier gas stream of the chromatograph under controlled conditions that is, in a substantially unaltered state with minimal changes in pressure and temperature prior to analysis as compared to analysis following transfer of a formation fluid sample to the surface. Analysis may also be conducted above the bubble point pressure of the fluid to maintain a single phase for analysis and thus avoid the problems of phase separation.

The formation fluid sample should be subjected to analysis after identifying that the sample is representative of the formation fluid. A location for sampling may be selected with reference to this criterion. The term "formation fluid" is intended to encompass the native fluid of the formation ideally without any contamination by fluids, such as drilling muds, not naturally present in the formation.

Identifying the representative nature of the sample of the formation fluid is based on monitoring a signal from a sensor; or an array of signals from various sensors. The various sensors include at least one and preferably more of conductivity, resistivity, temperature, flow-rate, pressure and density sensors. Signals from the selected sensors are transmitted in real time to the surface where an operator or control unit determines representativeness of the formation fluid sample. The operator or a control unit may determine the best time and means to obtain a truly representative formation fluid sample. Consistency of sensor signals indicates sample representativeness. However, the signals from the sensors also assist in identifying components and characteristic properties (pressure, temperature, conductivity, density etc) of the formation fluid(s).

Resistivity or conductivity data alone does not allow positive identification of hydrocarbons and, further, stability of resistivity measurement is not a sufficient condition for sample representativeness. For example, a low salinity (fresh) formation water will present a high resistivity or low conductivity which may provide a false positive identification of hydrocarbons. Additional measurement of density provides: (1) a contrast to identify hydrocarbons which typically have a density of less than water, (2) ability to clearly distinguish oil from gas.

The commencement of chromatographic analysis at the location may also be made contingent on measurement of mobility (the ratio of rock permeability to fluid viscosity) and comparison of the trend with that as sensed by pressure sensors. When such indications show that the fluid sample is representative, chromatographic analysis commences. The analysing step, occurs without requirement for samples to be brought to the surface. Sampling may also be conducted above the bubble point pressure by increasing the pressure of the sample.

The sample may be injected directly into the chromatograph which may be configured for gas, liquid or both forms of chromatography. However, it may also be introduced in admixture with a carrier gas.

The method allows analysis of hydrocarbon fluids containing hydrocarbon species including species containing sulphur and other elements. The hydrocarbon species may have carbon number up to $C_{40}$. A specific column may be designed for $C_{12}$ to $C_{22}$ hydrocarbon species. Other specific columns may be adapted to the analysis of other specific carbon number fractions. Multiple columns may be used for simultaneous analyses of specific molecular fractions. The same column may be operated at different temperature, or under different conditions, to enable the column to be used to analyse various species present in formation fluid samples.

The method may be used to determine fractions of sulphur containing compounds such as mercaptans. Inorganic He, Hg, $H_2S$ and $CO_2$ fractions in the formation fluid may also be determined. The chromatographic analysis may be used in combination with other analytical techniques, such as Mass Spectroscopy or Raman Effect spectroscopy, each technique being selected with a view to the desired accuracy of the analysis for given species within a formation fluid. Such combination of analytical techniques is aimed at better evaluation of a reservoir.

In a further aspect of the invention, there is provided an analytical tool for downhole analysis of properties of fluids contained in a geological formation including:

a) a housing;

b) a chromatograph robust to downhole conditions; and c) a collection means for extracting a formation fluid sample from a location within the geological formation and delivering the sample to the chromatograph;

wherein the collection means is arranged to deliver a controlled formation fluid sample to the chromatograph with or without admixture with a solvent.

The housing, which is designed to cope with high pressure and temperature conditions as well as robust handling conditions downhole, includes sensor(s) to determine whether a formation fluid sample is representative of the formation fluid within the geological formation. Such sensor(s) may also produce data important to evaluation of the geological formation.

The sensor(s) may include one or more of resistivity, conductivity, temperature, flow-rate, pressure and/or density sensors. Signals from the selected sensor(s) are analysed to determine whether the sample is representative of the formation fluid. The signals from the sensors may also be used to identify the components and properties of the formation fluid.

The tool may be used for other purposes than compositional analysis. To that end, the tool housing may include instruments and sensors for other purposes. For example, the tool may be provided with a range of sensors including conductivity, density and resistivity sensors. Flow, temperature and pressure sensors may also be included to identify important characteristics of the formation fluid and to discriminate against borehole fluid filtrate contamination.

Figure 2:
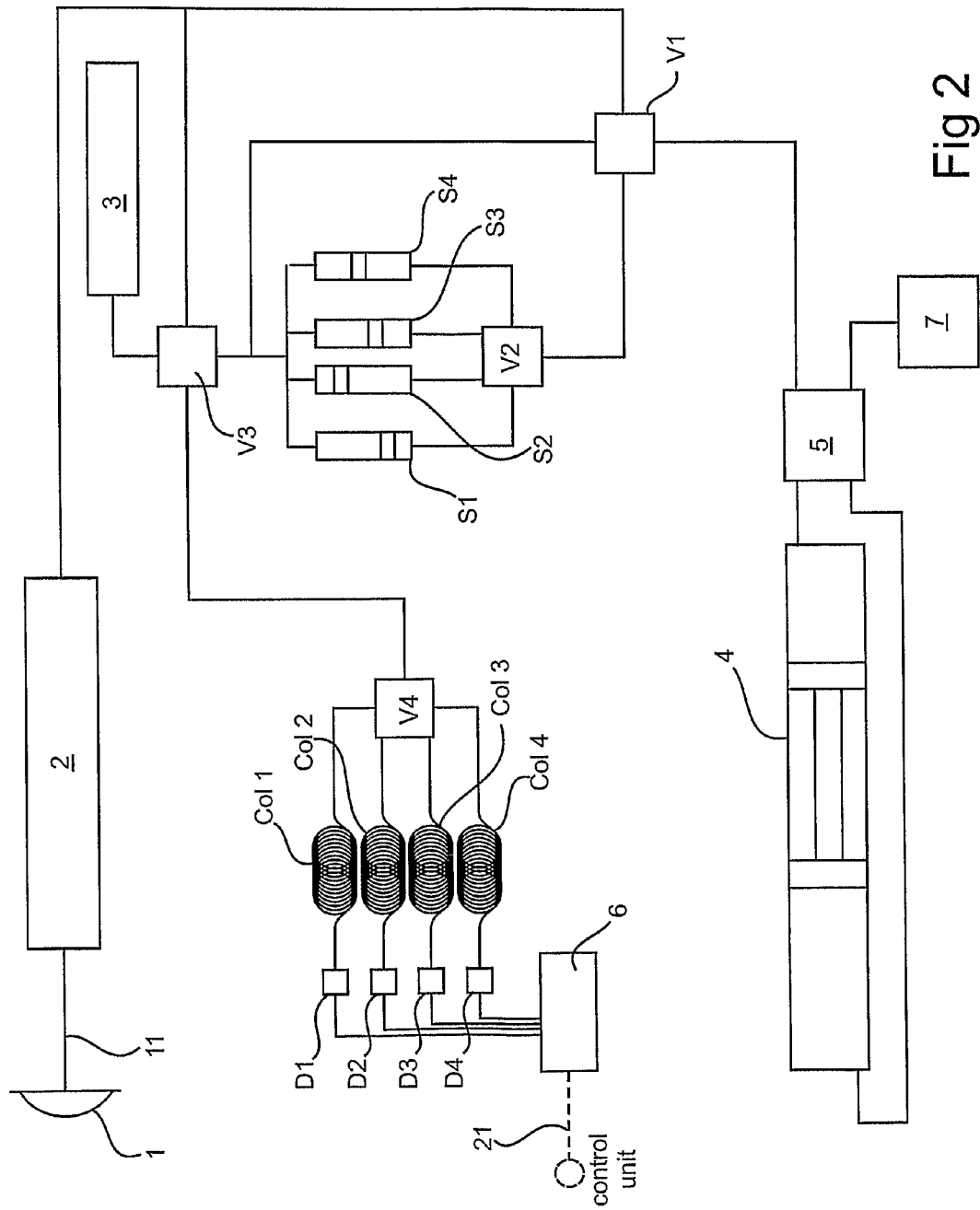

The analytical method and tool of the invention will now be described with reference to preferred embodiments thereof, made with reference to the following drawings in which:

FIG. 1 shows a schematic of a borehole made during exploration for oil and gas using the method in accordance with one embodiment of the present invention; and FIG. 2 shows a schematic flowchart of a downhole tool for analyzing fluid composition in accordance with one embodiment of the present invention.

Referring to FIGS. 1 and 2, there is shown a borehole 10 drilled through a geological formation or reservoir 30 during exploration for oil and gas. Borehole 10 is shown as vertically extending but this is not intended to be limiting. Present within the borehole 10 is a sampling tool 20 for sampling composition and other properties of formation fluids, especially hydrocarbon fluids, at various locations within the borehole 10 and, it follows, within geological formation 30. Sampling tool 20 is here illustrated as sampling at location 10a of the borehole 10. Analysis of fluids present within geological formation 30 is provided by sampling at location 10a and other selected locations within borehole 10. The sampling tool 20 is a wire-line pump-through tool with wire-line 21 used to convey electrical signals (data) between the surface 65 and sampling tool 20. The electrical signals may also be sent to and from a control unit (not shown) for sampling tool 20. The control unit may be geographically remote from the borehole 10.

The sampling tool 20 has a housing 22 in which is located a gas/liquid chromatograph 24. Housing 22 is of robust material selected and fabricated to resist high pressure and temperature conditions of borehole 10 as well as robust handling downhole. Chromatograph 24 includes four sampling columns Col1-Col4, some adapted for gas chromatography and others adapted for liquid chromatography.

The chromatograph 24 includes a number of calibration standards S1 to S4 which may be selected according to the species present in the geological formation to be analysed, description of standards being—for example—as provided below for the chromatographic columns. However, the standards S1 to S4 could include species not present within the formation fluid, for example, chloroform.

The operation of the gas chromatograph is conventional and those skilled in the art of chromatographic analysis will understand the nature of the technique which is also described in Pat JF Sandra, "Basic Principles of Chromatography" "Gas Chromatography", and "Liquid Chromatography". Ullmann's Encyclopedia of Industrial Chemistry, Vol. B5, VCH, Weinheim (1994), pp 155-301, the contents of which are hereby incorporated herein by reference. The sample tool 20 with chromatograph 24 is set into a desired downhole position at location 10a. Samples of formation fluids are then induced, due to pressure differential effects, through sample pad 1 located in contact with the bore hole 10 wall and into sampling tool 20. The sample pad 1 has a duct 11 communicating with a fluid sensor assembly 2 fitted with various sensors including resistivity, conductivity and fluid density sensors for sensing these properties in a fluid sample in real time. The fluid sensor assembly is connected to a valve, V1, which isolates the gas chromatograph module of the instrument from the fluid circuit.

Formation fluid samples are not introduced to the chromatograph 24 until preliminary measures, assessing sample representativeness, have been taken. To this end, a sensor assembly fitted with resistivity, conductivity and fluid density sensors, is provided. These sensors provide signals that are sent to the surface 65 for recording and display allowing the operator of the sampling tool 20 to control operation of the sampling tool 20, and specifically chromatograph 24, to achieve accurate analyses of the formation fluids. Sampling tool 20 may be adapted to tasks other than chromatographic analysis and the operator controls the sampling tool 20 to perform those tasks.

The operator monitors a number of hydrocarbon fluid samples and, when a consistent signal from each of the resistivity, conductivity and fluid density sensors is provided, determines that the formation fluid sample is representative.

Once the operator determines that a representative fluid sample is available, the chromatograph 24 is set into position and operated to analyse fluid sample composition. The chromatograph 24 can be used to determine the characteristics of hydrocarbon species, particularly in the carbon number range up to $C_{40}$ and other species, such as helium, mercury, $H_2S$ and sulphur containing compounds such as mercaptans, within the geological formation 30. For example, the sampling tool 20 allows the fractions of various hydrocarbons present within the formation fluid sample to be determined. Such measurements are used to allow commercial evaluation of the prospects of the formation for production and/or further exploration. A computer model receiving signals or data indicating properties—such as reservoir pressure and temperature—and compositional data, for example for the hydrocarbon fractions and so on, may be used to assist in the commercial evaluation and the provision of safety measures if $H_2S$ or mercury is present. The data may be processed, by the computer model, in any desired manner and may be displayed for ready understanding. A graphic display of the chromatographic data may allow the compositional data to be readily evaluated, both qualitatively and quantitatively in the manner as described in Pat JF Sandra, referenced above.

The chromatograph 24 is calibrated, also downhole, using standards as contained in standard sources S1 to S4. During calibration, specific standards, for example for analyte hydrocarbons, that is, hydrocarbons likely to be present in the formation fluids, are injected into the chromatograph 24 and the response recorded. Formation fluid samples are also analysed once found to be representative. Quantitative analysis is achievable by comparison of the responses for standards and formation fluid samples.

Once calibrated, the chromatograph 24 is ready for use in analysing formation fluids. V1 is opened and fluid flow is diverted through it. Fluid pump 4 can then positively displace the representative sample through V3 and back to the flow line. In this manner, fluid pressure may be kept above the bubble point pressure to maintain a single phase for accurate analysis. The formation fluid sample may then be injected directly into a carrier gas flow from gas supply assembly 3 at or above reservoir pressure, pressure being controlled, if necessary, to achieve this. The analysis occurs at temperature variable with the species being analysed. That is, higher column temperatures may correspond with analysis for higher homologs or carbon numbers. Lower column temperatures may correspond with lower homologs or carbon numbers. One column could therefore serve two functions, if temperature controlled. The column selection valve, V4, then diverts the sample and carrier gas through the appropriate column, (Col1-Col4), for which analyses are requested. By way of example, the columns could be employed for analysis as follows:

Col1 light hydrocarbons, $C_1$-$C_{10}$
Col2 light and medium hydrocarbons, $C_1$ to $C_{40}$
Col3 analyses similar to PONA (paraffin, olefin, naphthalenes, aromatics)
Col4 gas and trace elements, $C_1$, $CO_2$, $H_2S$ and Hg
Col 1 will operate at generally lower temperature than Col 2.

A detector D1, D2, D3, D4 associated with each requisite column then records and prepares the data for transmission to the surface 65 from data acquisition unit 6 by wireline 21 in real time. The data may be processed to characterise the composition and nature of the formation fluid, assisting in the reservoir evaluation and exploration process, The data may be displayed on a computer screen or other display unit for ready evaluation.

After hydrocarbon fluid sample analysis, the chromatograph 24 is returned to standard mode and standard mixtures from standards S1 to S4 are passed through the chromatograph 24. The availability of four standards allows sufficient modes of calibration to ensure proper operation of the equipment and reference retention times to ensure proper identification of the hydrocarbon components. However, a different number of standards could be selected. Sample testing may be repeated to ensure repeatability and veracity.

The chromatograph 24 can be flushed with the representative fluid once sampling and the standard check has been performed to ensure that each test sample is free from contamination and ready for further analysis.

Following an analysis stage at one level or location 10a of the borehole 10, sampling tool 20 may be moved to a different location in borehole 10 where the tool is reset and the sampling analytical process is repeated. In this way, a thorough characterisation of the formation fluids and, thus, the geological formation 30 may be achieved without the kind of errors caused through surface sample transfer and surface analysis or changing of sample properties.

By way of example, the gas chromatograph of the present invention has been used to analyse hydrocarbon species up to $C_{40}$. Concentrations of hazardous species such as $H_2S$ and Hg may also be analysed, such data being important to safety, and hazard evaluation of the geological formation fluids.

Chromatographic data may support, or be confirmed by, data obtained from other sample analysis methods such as for compartmentalized reservoirs where the fluids in each compartment are different. Selection of locations for sampling may be selected having regard to reservoir compartmentalisation.

Modifications and variations to the analytical method and tool of the invention may be apparent to the skilled reader of this disclosure. Such modifications and variations are deemed within the scope of this disclosure. For example, the nature of the standards or specific columns may be varied dependent on the formation being explored.

The invention claimed is:

1. A method of analyzing properties of fluids contained in a geological formation including the steps of:
   a) lowering a tool containing a chromatograph down to the geological formation;
   b) setting the tool;
   c) extracting a sample of fluid from the geological formation under controlled conditions and directing it into the chromatograph after identifying that the sample is representative of the formation fluid based on monitoring an array of signals from various sensors for consistency; and
   d) analyzing the composition of the formation fluid sample downhole;
   wherein the chromatograph has a plurality of gas chromatography columns for analyses of specific molecular fractions and inorganic species present in the formation fluid sample and wherein each column of said plurality of gas chromatography columns is operated under different conditions to enable the column to be used to analyze various species present in said formation fluid sample.

2. The method of claim 1 wherein each column of said plurality of columns is operated under different temperature conditions.

3. The method of claim 1 wherein the formation fluid sample is introduced directly to the chromatograph, or to a carrier gas stream of the chromatograph in a substantially unaltered state.

4. The method of claim 1 wherein the formation fluid sample is analyzed above the bubble point pressure of the fluid to maintain a single phase for analysis.

5. The method of claim 1 wherein identifying the representative nature of the sample of the formation fluid is based on monitoring the array of signals from the various sensors.

6. The method of claim 5 wherein the various sensors are selected from the group consisting of conductivity, resistivity, temperature, flow-rate, pressure and fluid density sensors.

7. The method of claim 6 wherein positive identification of hydrocarbons is determined based on assessment of resistivity, conductivity and fluid density data.

8. The method of claim 1 wherein identifying the representative nature of the sample of the formation fluid is based on monitoring the array of signals from the various sensors transmitted in real time to the surface.

9. The method of claim 8 wherein the various sensors are selected from the group consisting of conductivity, resistivity, temperature, flow-rate, pressure and fluid density sensors.

10. The method of claim 1 wherein organic sulphur containing compounds are analyzed.

11. The method of claim 10 wherein said organic sulphur containing compounds are mercaptans.

12. The method of claim 1 including analyzing to determine at least one inorganic species selected from the group consisting of He, $H_2S$ and $CO_2$ fractions in the formation fluid.

13. An analytical tool for downhole analysis of properties of fluids contained in a geological formation including:
   a) a housing includes a plurality of sensors to determine whether a formation fluid sample is representative of the formation fluid within the geological formation;
   b) a chromatograph located within the housing; and
   c) a collection means for extracting a fluid sample from the geological formation and delivering the sample to the chromatograph downhole;
   wherein the chromatograph has a plurality of gas chromatography columns for analyses of specific molecular fractions and inorganic species present in the formation fluid sample
   and wherein each column of said plurality of gas chromatography columns is operable under different conditions to enable the column to be used to analyze various species present in the formation fluid sample.

14. The analytical tool of claim 13 wherein each column of said plurality of columns is operated under different temperature conditions.

15. The analytical tool of claim 13 wherein the plurality of sensors include one or more of resistivity, conductivity, temperature, flow-rate, pressure and/or density sensors, signals from the selected sensors being analyzed to determine whether the sample is representative of the formation fluid.

16. A method of analyzing properties of fluids contained in a geological formation including the steps of:
   lowering a tool containing a chromatograph down to the geological formation;
   setting the tool;
   extracting a sample of fluid from the geological formation under controlled conditions and directing it into the chromatograph downhole after identifying that the sample is representative of the formation fluid; and
   analyzing the composition of the formation fluid sample downhole
   wherein the chromatograph has a plurality of gas chromatography columns for analysis of specific molecular fractions and inorganic species present in the formation fluid sample and wherein the formation fluid sample is analyzed above the bubble point pressure of the fluid by increasing the pressure of the sample to maintain a single phase for analysis.

* * * * *